(12) United States Patent  
Griffin et al.

(10) Patent No.: US 7,909,817 B2
(45) Date of Patent: Mar. 22, 2011

(54) LATERAL LASER FIBER FOR HIGH AVERAGE POWER AND PEAK PULSE ENERGY

(75) Inventors: Stephen E. Griffin, Glendale, AZ (US); Teresanne Griffin, Glendale, AZ (US)

(73) Assignee: Innovaquartz, Inc. (AMS Research Corporation), Minnetonka, MN (US)

(*) Notice: Subject to any disclaimer, the term of this patent is extended or adjusted under 35 U.S.C. 154(b) by 1566 days.

(21) Appl. No.: 11/148,817

(22) Filed: Jun. 8, 2005

(65) Prior Publication Data

US 2006/0282068 A1    Dec. 14, 2006

(51) Int. Cl.
*A61B 18/18* (2006.01)
(52) U.S. Cl. .......................................... 606/13; 606/17
(58) Field of Classification Search .......... 606/7, 13–18; 385/4, 15, 53, 73
See application file for complete search history.

(56) References Cited

U.S. PATENT DOCUMENTS

| 5,246,436 A | 9/1993 | Rowe | 606/13 |
| 5,428,699 A | 6/1995 | Pon | 385/31 |
| 5,772,657 A * | 6/1998 | Hmelar et al. | 606/15 |
| 5,957,917 A * | 9/1999 | Doiron et al. | 606/15 |
| 6,802,838 B2 | 10/2004 | Loeb et al. | 606/13 |
| 7,063,694 B2 * | 6/2006 | Nahen et al. | 606/15 |

* cited by examiner

*Primary Examiner* — Ahmed M Farah
(74) *Attorney, Agent, or Firm* — Kimberly K. Baxter; Gregory L. Koeller (57) ABSTRACT

An improved optical fiber comprising a waveguide with an input for coupling focused laser energy into the waveguide and communicating electromagnetic radiation in a propagation direction to an internally reflective tip of the waveguide, a tissue contacting surface wherein the light path from the reflecting surface to the transmitting surface in substantially homogenous in refractive index and cooled by fluid flow. In minimizing the variations in refractive index within the lateral light path, while providing active cooling directly below the tissue contact surface, the invention prevents internal reflections and beam distortion and greatly improves the efficiency and durability of the laterally directing probe. Free rotation of the tissue contact surface, about the lateral tip, may be provided and tissue vaporization efficiency may be improved by providing a morcellating tool on the tissue contact surface.

11 Claims, 10 Drawing Sheets

FIGURE 1a    PRIOR ART, ABE, ET AL.    FIGURE 1b FIGURES 2B    PRIOR ART    FIGURE 2A FIGURE 3a  PRIOR ART  FIGURE 3b

FIGURE 4  (PRIOR ART, SAADAT, ET AL.)

FIGURE 6     (PRIOR ART, BREKKE)

FIGURE 7     (PRIOR ART, GRIFFIN)

FIGURE 21

LATERAL LASER FIBER FOR HIGH AVERAGE POWER AND PEAK PULSE ENERGY

FIELD OF THE INVENTION

The present invention relates generally to applications of lasers to endosurgery and specifically to delivery of high energy density or high average power to tissues located about body lumen, such as the prostate gland about the urethra.

BACKGROUND OF THE INVENTION AND DESCRIPTION OF THE PRIOR ART

Treatment of benign prostatic hypertrophy (BPH) with laser energy has a somewhat checkered past, but in recent years advances in the understanding of laser-tissue interactions and laser design have enabled realization of much of the promise of the initial concept. The longstanding "gold standard" for surgical treatment of benign enlarged prostate glands is a technique called TURP: Transurethral Resection of the Prostate. In TURP procedures, an electric current is passed through working tips of various shapes, heating them to permit tissue to be selectively carved or charred away. While TURP is widely used with good clinical results, significant bleeding is common and the procedure can be time consuming, particularly where the glands are large. Post-operative swelling of tissues remaining post-TURP requires catheterization to permit release of urine and hospital recovery can be protracted. Post-operative pain is often prolonged and complications such as bladder neck strictures and nerve damage are relatively common, leading to a fairly high incidence of retrograde ejaculation, incontinence and temporary impotence among patients.

The VLAP procedure of the 1990s (Visual Laser Ablation of the Prostate) promised solutions to the problems with TURP, but the dominant laser wavelength (1064 nm) penetrated too deeply into the prostate tissue such that deep coagulation (tissue death but not removal) resulted and non-target tissues were often damaged inadvertently. Fluid uptake in these damaged tissues caused post-VLAP complications and it was difficult for surgeons to judge the actual degree of tissue death that would result beneath the surface treatment.

Contributing to this problem was the broad spectrum of lateral fiber function, with fibers manufactured by as many as two dozen companies. With no established minimum performance standards, most lateral emitting fibers of the period delivered relatively diffuse energy with significant scattered radiation such that tissue effects varied widely from surgery to surgery. The vast majority of urologists who experimented with VLAP in the 1990s, and various modifications thereof, abandoned the method and returned to TURP by about 1996.

More recently, a new technique called PVP (Photo Vaporization of the Prostate) has spearheaded resurgence in applications of lasers to BPH surgery, driven more by patients than by the Urological Specialty, for the reportedly very low incidence of side effects. The technique uses 532 nm light that is strongly absorbed by hemoglobin such that surface vaporization of tissue is the dominant affect. In addition, the lateral fiber used in the procedure (GreenLight™, U.S. Pat. No. 5,428,699, referenced below as prior art) is more efficient than most that were available in the 1990s such that high energy density spots are presented to tissue with little damaging scatter. Also contributing to the overall high performance of the system (laser plus fiber combination) is the inherently high energy density of the laser itself, as taught by U.S. Pat. No. 6,554,824, (Davenport, et al.). With an average of 80 W of 523 nm light provided to the fiber, approximately 70 W is delivered laterally to the target tissue within a small diameter, substantially circular. The output spot energy profile produced is such that substantially all of the illuminated tissue is vaporized.

The PVP procedure is popular with patients and surgeons because it fast, essentially painless (no prolonged, post-operative tissue sloughing), offers immediate relief (often no catheter is required beyond initial recovery), generally requires no hospital stay and has a very low incidence of complications. Such surgeries should also be popular with private and government insurers in that the overall costs associated with treatment are considerably lower for PVP than for TURP in most cases.

While enlarged prostate glands of typical size (30 grams) may be treated sufficiently within as little as 15 minutes with PVP, larger glands prove problematic. As the surgery proceeds, the output "cap" of the lateral fiber degrades: the surface through which the laser light passes becomes opaque or "frosted", scattering light. The damage accelerates with continued use and eventually the erosion at the surface extends completely through the cap and surgical irrigation fluid leaks into the cap as it heats and cools with each laser pulse.

Since the redirection of light within lateral fibers such as this is based upon total internal reflection (TIR) due to refractive index differences of the fiber core and the air trapped in the protective cap, influx of aqueous solution at a refractive index more similar to the glass than to air disrupts this condition and the fiber fails by firing axially. Such failures can be catastrophic, with uncontrolled laser emission causing bladder neck damage or bladder or urethral perforation. As a minimum inconvenience, at least two GreenLight™ fibers may be required for large glands resulting in delays and added surgical costs.

A competing technique is also gaining some ground: HoLAP or Holmium Laser Ablation of the Prostate. In theory, the holmium wavelength is even more favorable than KTP (532 nm mentioned above, or frequency doubled Nd:YAG) for controlled tissue affect with stronger absorption resulting in even less underlying coagulation. In addition, procedural problems and cost issues with the PVP can be avoided. The bright green KTP laser emission interferes with vision requiring special endoscope camera filters and orange safety goggles for surgical staff and the frequency doubled, 200 W Nd:YAG laser requires non-standard electrical power (50 A, 208 VAC) and high flow cooling water. The KTP laser is costly (~$80,000) and is currently a "single procedure box", meaning only BPH surgery is done with the appliance, and GreenLight™ fibers are extremely expensive for a disposable device at US $875 each. In contrast, the holmium laser is competent in treating other urological and non-urological conditions from kidney stones to ruptured spinal discs. It would be desirable to provide high performance lateral fibers at reasonable costs for holmium lasers for providing lower cost laser BPH surgery to a broader population.

In the PVP procedure, considerable effort and expense has been expended in producing lasers (Davenport, et al.) and fiber delivery systems (Pon) that minimize irradiation of tissue with low energy density light in that the lower energy densities may cause deep thermal damage without immediate tissue removal. This is not a new observation. Beginning in 1989, the author of the current art personally has experienced laser injuries from a broad range of laser wavelengths and energy profiles and has long noted that higher energy density injuries heal much more rapidly than low energy density injuries, with negligible collateral tissue damage, regardless of the laser wavelength. Unfortunately, in spite of the high energy density light produced by the KTP laser taught in Davenport, the degradation in performance of the fiber taught in Pon is such that the proportion of low energy density light delivered to the tissue steadily grows as the procedure proceeds.

Holmium energy is strongly absorbed by water and is absorbed to a lesser degree by other tissue components, including blood, so where the PVP laser becomes less effective as surface tissue is ablated and underlying tissue are blanched of blood, the holmium continues to work with high efficiency. Owing to the stronger absorption of the holmium laser energy by tissues, the depth of laser energy penetration for the holmium is even lower than that for KTP, so unwanted deep tissue death has the potential to be reduced even further, if high energy density can be reliably delivered to the target tissues over the course of the procedure.

The barriers to holmium applications in BPH are minor but persistent. Protective cap degradation appears to be more pronounced with the holmium wavelength than with KTP, possibly due to a higher degree of interaction of the light with the cap material (silica), the high pulse energy density and the considerable heat generated by interactions of the laser energy with the aqueous irrigation fluid and tissues. In particular, water attacks the hot silica through hydrothermal erosion. This is complicated (and accelerated) by devitrification of the surface that is catalyzed (at elevated temperatures) by ions commonly found in tissues and irrigation fluids: alkali and alkaline earth metal ions such as sodium (I) and calcium (II).

The photo-thermal and/or photo-acoustic shock waves that are generated by the laser pulses in the glass and in the water are so intense that caps of similar dimensions to those used in the PVP fiber can simply shatter to dust at average powers of 40 W or more. Thicker caps resist this damage but remain susceptible to erosion failures in apparent excess of that seen in PVP. (Much of the erosion problem could be surgical technique related, in both procedures, e.g. some surgeons may hold the holmium fiber in closer proximity to tissue than KTP fibers and some may clean the fiber tip intra-operatively while others may not.)

Further, the energy density profile of holmium lasers contains a broader mix of modes than that produced by the KTP laser used in the PVP procedure. As taught by the author of the present art in U.S. Pat. No. 6,282,349 (Griffin) and other publications, holmium lasers are notorious for thermal lensing problems within the lasing medium, resulting in variable mode output beam profile. This broader distribution presents areas of the beam profile that are not of sufficient energy density to cause tissue vaporization and undesirable coagulation is the result. Reducing the high order modes produced by the laser itself by reducing the heating that the pump energy produced in the laser medium, as taught in Davenport, is not the sole means of minimizing this problem, nor is it the most economical or logical means. The higher order modes may be selectively excluded from coupling to the surgical fiber (mode stripping), or preferably, the higher order modes may be converted to lower order modes within the energy delivery fiber, at the laser-to-fiber coupling or at the fiber output.

The energy density profile at the fiber output surface is not only critical for achieving the desired tissue response, but for prolonging the fiber performance. Energy densities presented at the fiber output that are insufficient for tissue vaporization promote tissue adhesions to the fiber tip. Adhered tissues give rise to conditions that promote acceleration of performance degradation. GreenLight™ fibers modified for use on holmium lasers function very well in comparison to other fiber designs, indicating that the superior efficiency of the fiber output is critical to clinical function.

A less efficient fiber design, the (DuoTome™), is sole holmium fiber that is capable of delivering average holmium power equivalent to the GreenLight used with the KTP laser, but it requires a 100 W input to achieve vaporization rates similar to the GreenLight/PVP procedure. At 100 W input, the DuoTome output spot presents lower energy density to tissue than does the GreenLight due to more scatter and cylindrical lens distortion within the lesser fiber design such that, even given the superior absorption of holmium energy by target tissues, more coagulation results than is clinically desirable or necessary.

Inefficiency breads excess heat at the fiber tip, which promotes tissue adhesions and fiber damage, so fibers are even more prone to premature failure in holmium BPH treatment than they are in PVP. Surgical progress is not quite as rapid nor are target tissues quite as precisely ablated. Further, energy density in the fiber output spot is critical to successful vaporization without significant concomitant damage to critical, non-target structures near the site of therapy.

The DuoTome™ avoids irradiating non-target tissues (with the scattered laser light in the output) by sheathing the cap in stainless steel. Only a tiny window is presented for the laser energy to escape. As a consequence of trapping the undesirable energy within the steel enclosure the fiber tip gets hot in use and hot steel can also cause unwanted tissue damage and complications. Furthermore, the stainless steel containment sacrifices protective cap thickness in an application where total diameter is limited by the size of the working channel provided within the endoscopic device. The maximum diameter limit for the smallest working channel (7.5 Fr.) in rigid cystoscope/resectoscopes is ~2.45 mm where compatibility with most flexible cystoscopes (presenting working channels as small as 6 Fr.) the maximum diameter for the device is ~1.75 mm and the length of rigid section (typically the cap) should not exceed ~12 mm least the device not easily pass the channel in moderate deflection.

At least two other fiber designs have been tried with the holmium lasers, as taught by Griffin and Brekke, referenced below. Both are high efficiency designs that utilize fiber-to-cap fusion to minimize scatter. Both fail at approximately 40 W through catastrophic disintegration. It is thought that the residual stress concentrations in the fiber-to-cap fusion region likely render the fused fibers more susceptible to the thermal shocks encountered in the surgery than non-fused fibers.

All current art lateral fibers based upon total internal reflection (TIR) at tips—polished at the critical angle as defined by Snell's Law as opposed to external reflector designs such as U.S. Pat. No. 5,242,437 (Everett)—that are designed for surgeries such as prostate resection suffer the opacity at output failure mode, where the glass surface in contact with tissue and/or irrigation fluid and/or bodily fluids degrades through hydrolysis and devitrification. Even minor degradation of the output surface quality causes difficulties in surgery. There is typically a coaxial, visible laser wavelength transmitted within the optical fiber that serves the surgeon in orienting the fiber output properly on target tissues: the "aiming beam". As the output surface degrades, so the clarity of the aiming beam degrades, making precise orientation more difficult.

Accordingly, fibers are also equipped with accessory "orientation markers" that are typically proximal to the output area, generally opposite the fiber output such that they may be visualized when the fiber is properly positioned, pointing generally at tissue rather than generally at the surgeon or endoscopic equipment. These markers are usually ink printed lines or text on transparent heat shrink tubing that are carefully positioned with respect to the fiber output during assembly. As the fiber continues to degrade with use, it becomes more inefficient such that more laser energy is consumed in heating the device, causing more tissue adhesions, more energy absorption and more glass degradation, i.e. the degradation progress is governed by second order kinetics and accelerates. As the output tip heats to greater and greater temperatures, the thermally labile orientation marker becomes damaged, further reducing the ability of the surgeon to properly orient the fiber output.

Where temperatures rise even further, adhesives used to secure the protective cap to the fiber fail, or the fibers' polymer buffer coatings themselves fail, and the cap may dislodge. A dislodged cap is a catastrophic failure (axial emission) and often requires prolonged expeditions within the urinary tract for the purpose of retrieving the loose cap.

In summary, heating of glass tipped fibers in use results in multiple problems far in excess of increasing the depth of tissue death beyond the therapeutic necessity. Elevated temperatures greatly accelerate catalytic devitrification of the silica dissolution surface, resulting in loss of surgical orientation. Reduced surgical efficacy and precision result for increasing scatter at fiber output. Adhered tissues absorb scattered laser energy and carbonize. Carbonized tissues absorb even more laser energy and may reach temperatures in excess of 750° C. at the protective cap surface. Larger temperature differentials in the low thermal conductivity silica material may produce stresses sufficient to cause fracture.

It would be desirable to address the failure modes and inefficiencies of side fire fibers to permit use with widely deployed lasers to achieve clinical results similar to, and theoretically superior to those achieved with the GreenLight™/PVP procedure, as measured by clinical outcome and speed of surgery, with better ease of use and lower costs. It would also be desirable to improve the performance of the fiber used in PVP and, for that matter, any surgery that is enabled or facilitated by fibers that emit radiation lateral to the fiber axis.

Rowe (U.S. Pat. No. 5,246,436) discloses a low hydroxyl fused silica fiber optic with a metal coated tip, with an opening designed to leak energy in a generally lateral direction that is housed in a hollow tube possessing an opening corresponding to the location of the radiation leak through which cutting energy is to pass. The tip is irrigated by fluid transmitted by one lumen and aspirated by a second lumen. According to Rowe, because the laser energy is highly absorbed by water (the main component of the cooling fluid and the target tissue), air bubbles formed by the laser pulses at the fiber tip permit irreproducible and uncontrolled energy coupling to delicate target tissues.

The fluid flow is designed to sweep those bubbles away as they are formed, providing improved control of laser to tissue interactions. It is unclear if the laser energy exiting the opening in the hollow tube surrounding the fiber tip, or hot gas bubbles formed by the laser energy that are permitted brief contact with tissue, or both, are intended to do the surgical work. Regardless of the intended mechanism, laser energy and fluid are in direct communication with the target tissue in Rowe.

While not specifically addressed in Rowe, the low [OH⁻] fused silica fiber taught is not terribly transparent to the mid-IR energy produced by the Er:YAG laser of the preferred embodiment such that, for the device to function at all, the entire fiber length can not be more than several centimeters. The lateral tip design disclosed in Rowe is also inefficient as much of the laser energy that does manage to reach the lateral tip will convert to heat in multiple reflections therein. Given the delicate surgery addressed by the Rowe design, these inefficiencies may well be intentional, or at least acceptable, but this does not alter the fact that such a design could not possibly function to in major surgery, such as prostate resection by Er:YAG infrared energy as disclosed herein. Further, due to the encapsulated volume within which the Rowe device must function, it requires two fluid conduits with metered inflow and metered aspiration of irrigation fluid to prevent inflation or collapse of the eye in use.

Similarly, U.S. Pat. No. 6,802,838 (Loeb, et al.) discloses a device intended to be inserted "interstitially" into tissue, where net fluid flow to or from the target tissue is known to be problematic in the surgical art. Loeb, et al. discloses a more traditional lateral emitting fiber with a bevel tip that is encapsulated to preserve the refractive index barrier needed to cause the light to be redirected off axis (similar to the present invention and other prior art). Loeb, et al., also discloses the lateral fiber tip disposed within a hollow cylinder through which cooling fluid flows, but as in Rowe, Loeb, et al.'s primary purpose is not to cool the fiber tip, but the tissue. Again, there are at least two independent fluid channels within the hollow cylinder with fluid flow propelled by pressure and/or aspiration and both laser energy and irrigation fluids are in direct communication with the target tissue through the common opening (window). As in Rowe, Loeb, et al., further discloses that hot gasses generated by the laser interaction with tissue and irrigation fluids are swept away from the surgical site by the fluid flow, preventing excessive heating and suppressing unwanted, deeper coagulation (or other damage) in non-target tissue. Loeb, et al., does suggest that the fiber output may also be kept clean of contaminating tissue by the flowing fluids, but the inverse is true. By providing access to the optical output and further, by preferentially propelling loose tissues through that access port, the output surface is place in great jeopardy of contamination by tissues.

Similarly, U.S. Pat. No. 5,496,309 (Saadat, et al.) discloses a unidirectional fluid flow system about a light-redirecting prism in communication with the flat tip of an optical fiber. The prism is required to have substantially higher refractive index than the fluid to support reflection of energy in the lateral direction. The light redirection bevel is not formed on the delivery fiber since the fiber material is not of sufficiently higher refractive index. Again, the fluid flow and laser energy are in communication with the target tissue through a common, open port.

The likely reason for teaching an open port through which both laser energy and fluid flow pass or may pass, in Rowe, Loeb, et al., and Saadat, et al., is the prevailing opinion in the field that mid-infrared energy is so strongly absorbed by water that encapsulating a fluid thorough which IR energy passes will result in structural failures due to the expansion of rapidly vaporizing water. It is the thesis of this art that this is not the case.

Figure 20:
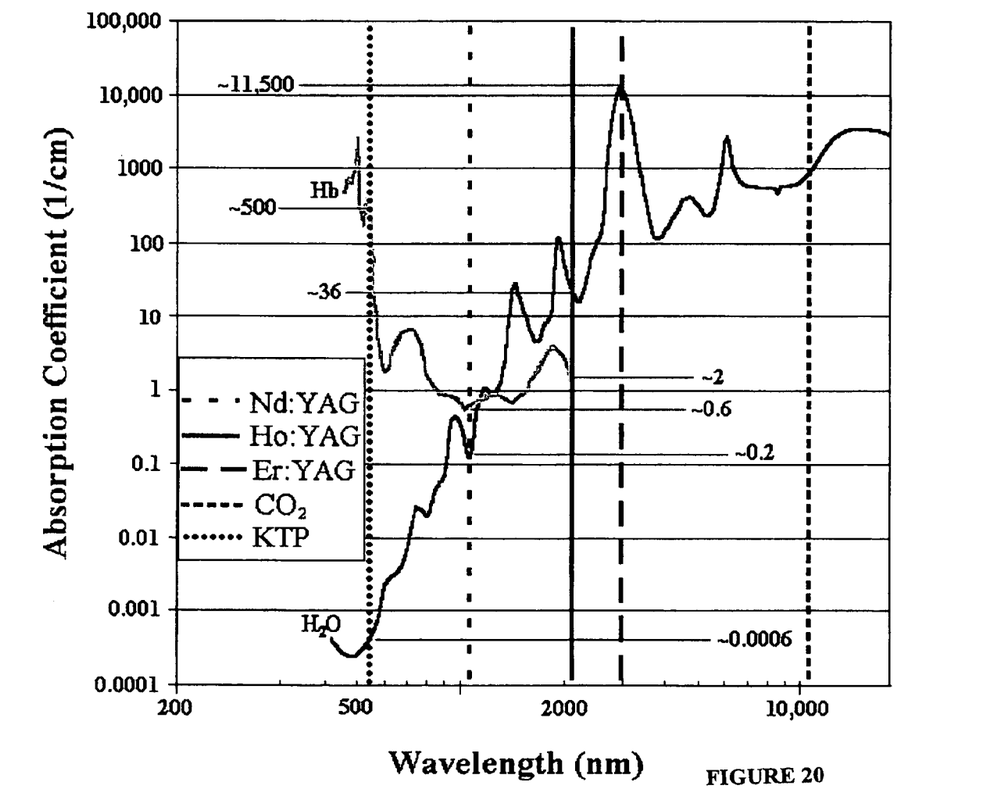
FIG. 20 is the absorption spectrum of water in the region of interest.

The absorption spectrum of liquid water shown in FIG. 20 clearly shows why Rowe teaches not to contain the water within a limited volume: the absorption coefficient of water at Er:YAG wavelengths is very large, meaning very little laser energy beyond the heat of vaporization is required to convert the water to steam. For Ho:YAG, however, the absorption coefficient is more than two orders of magnitude lower meaning the same volume of water would require more than 100-fold more laser energy to vaporize it. It is true that a fiber delivering holmium laser energy into a large volume of water creates bubbles (this bubble formation and collapse was thought to be the source of "acoustic shockwaves" for breaking-up kidney stones years ago, although the mechanism for holmium laser interaction with renal calculi is not known to be photochemical and thermochemical). Proponents of PVP suggest that this bubble formation robs the laser beam of sufficient energy to vaporize tissues. In surgery with holmium lasers, however, the simple fact of the matter is that large bubbles are not formed when the fiber is in close contact with tissue: the path length of travel through the water is not sufficient to absorb enough energy to change phase or such phase change is so limited that it has minimal impact.

Loeb, et al. and Saadat, et al. miss the opportunity to protect the optical surface of the lateral fibers by exposing them directly to tissue contact, most likely for the mistaken impression that to do otherwise is folly. Simply by capturing the fluid flow within a solid, but transmissive window, failure of the art taught in Loeb, et al. and Saadat, et al. would be greatly forestalled.

The fundamental mechanism of bi-directional fluid flow disclosed by Loeb, et al. and Rowe are similar, and both are designed to address similar surgical issues with respect to excess and uncontrolled heating of tissues by steam bubbles generated by the laser interaction with the irrigation fluid and tissues. Further, the laser and irrigation fluid are in direct communication with the target tissue through a common physical opening in the fluid flow-supporting hollow tube, exposing the critical optical output surface to direct contamination. The art disclosed herein utilizes unidirectional fluid flow to cool the tissue contact surface of the device where only laser energy is in direct communication with the target tissue. Cooling fluids exit the device through a remote port or ports formed expressly for that purpose and unidirectional flow greatly reduces the potential for tissue migration through a port to the optical output surface.

Accordingly, the unique strategy disclosed herein is to decouple functions that need not be coupled, thereby enabling optimization of each design for that function alone: the optical output and tissue contact surfaces are separated as are the laser energy and fluid output ports.

Fresnel reflections in lateral devices are a fundamental source of inefficiency, causing unwanted heating, tissue destruction and tissue adhesion. Where the light energy exits the sidewall of a fiber and enters the wall of the protective cap a portion of the energy reflected at each refractive index boundary. The amount of energy that is reflected is proportional to the difference in the refractive index differences acts the boundary as well as the light-to-surface contact angle. As Fresnel reflection increase in intensity with off-normal contact angles, it is desirable to minimize the angle that the worst case ray within a fiber will impart the cylindrical fiber outer diameter and the cylindrical protective cap inner diameter. More critically, in most prior art there are light-to-surface contact angles that exceed the critical angle as defined by Snell's Law, angles where all of the light will reflect rather than just a portion thereof, similarly to the desired 100% reflection provided by the bevel tips on the fiber termini.

Pon (U.S. Pat. No. 5,428,699) discloses a mechanism for reducing reflections within lateral devices by reducing the incident angles of the bulk of the light exiting the fiber cylindrical wall and entering the protective cap cylindrical wall to below the critical angle for reflection. This reduction may be accomplished as simply as utilizing a thicker than standard glass cladding layer over the fiber core. By providing a larger diameter where the light exits the side of the fiber, worst-case rays exiting near the edges of the core encounter much lower angles (relative to normal to the boundary tangent). Pon also teaches alternatives for further reductions in incident angles such as using square and triangular fiber segments at the bevel tip, to provide flat exit surfaces, and forming flat surfaces upon the thickened fiber cladding opposite the output.

Griffin (U.S. Pat. No. 5,562,657) and Brekke (U.S. Pat. No. 5,537,499) disclose another mechanism for reducing Fresnel reflections by substantially eliminating the large difference in refractive indices traversed by the emitted rays through fusion of the beveled fiber tip to the protective cap; through an intermediate layer of glass and directly, respectively. Griffin teaches a fused sleeve about the fiber at the output end, upon which composite the reflective bevel is polished. A subsequent fusion of the sleeved and beveled tip to the protective cap effectively eliminates all reflections by eliminating the air layer between fiber and cap. Brekke teaches direct fusion of the fiber output to the cap inner wall.

A further prior art design is disclosed in U.S. Pat. No. 4,740,047 (Abe, et al.). The Abe, et al. invention seeks to prevent misdirected laser energy from damaging patient tissue by including specially arranged reflective and antireflective coatings on the appropriate surfaces. The reflective and anti-reflective coating layers taught by the Abe, et al. patent, however, can melt or carbonize at high temperatures during use. Where the coating layers become damaged or carbonized, the degradation and failure cascade is initiated.

Abe, et al. further teaches flat surfaces within the device, but these flat surfaces are on the protective cap outer diameter where the cylindrical distortions are of far lesser concern than on the fiber outer diameter and cap inner diameter where the curvature is much higher and the refractive index difference in use (glass to air and air to glass) is much greater than for the outer diameter (glass to aqueous solution). While the flat output of Abe, et al. could be construed as an attempt to reduce light to surface angles and cylindrical distortions, in that it appears on both sides of the cap it was likely intended to permit the antireflective and reflective coatings to be applied and function independent of angular considerations.

Further compromises to performance result from the highly curved surfaces through which the laser energy must pass. Beyond causing significant scatter within the devices, these surfaces also act as lenses and distort the output profiles, resulting in a loss of energy density at the therapeutic site. These distortions are reduced by art taught in Pon, Griffin and Brekke, but riot in Loeb, et al. or Abe, et al.

Prior art that utilizes fluid flow does so with flow about the outer surface that is last traversed by the laser energy and is in direct communication with tissue. This arrangement is logical in that the fluid flows are intended to protect the tissue rather than the device. Fusion of fiber output surfaces to tissue contacting structures is used in prior art for reducing reflections (also known as scatter due to the complex refection patterns involved where myriad angles and curvatures are involved) and minimizing output spot distortions, but high residual stresses in the protective cap that can not be annealed (due to the presence of low thermal damage polymers in the structures) make fused fibers highly susceptible to the thermal shocks of high energy surgery, particularly pulsed holmium laser surgery.

Antireflective coatings are taught these purposes as well, but to limited effect in actual practice. Reduced contact angles, as taught by Pon, have the greatest practical effect in improving fiber performance, when carried out on the surface (s) where contact angles are highest, i.e. the fiber outer diameter and the protective cap inner diameter

SUMMARY OF THE INVENTION

The present invention provides design improvements to minimize reflections within the lateral output structure of surgical fibers, forestalling the onset of protective cap degradation and tissue adhesion, while improving the beam quality (energy density) of the lateral output profile for prolonged high performance lifetime in surgery and enabling precise direction of the vaporization of unwanted tissues without deep tissue coagulation and minimizing damage to important structures near the site of the therapy.

This is achieved in one embodiment by providing two separate protective caps that separate the functions that are in conflict in prior art: one (inner) cap for containing the gas (or vacuum) at the polished bevel surface that maintains the necessary refractive index difference for TIR, and a second cap to absorb the abuse of direct tissue contact. The inner cap may be just thick enough to protect the bevel tip, or thick enough to permit formation of a flat output surface without penetrating the fiber core. Complete cap penetration in erosion will not result in axial transmission as in all prior art in that the inner cap remains to protect the TIR condition, i.e. the new art provides double containment for added safety.

Additional protection may be provided by irrigation flow between the primary (gas containment) cap and the tissue contact cap. The fluid flow between the caps (intra-cap flow) serves well to cool the tissue contact cap from within and mainly serves to reduce the reflections and cylindrical distortions in the inner cap to outer cap transition by more closely matching the refractive index of glass. Flow is not intermittently disrupted due to intimate tissue contact and bubble formation as it is in the prior art and flow is provided for the purpose of preventing unnecessary heating in the device, as well as some cooling, as opposed to cooling the tissue. It is the thesis of this technology that device efficiency is of paramount import: to reduce, forestall onset or eliminate degradation improves surgical precision and speed, obviating the need of tissue-cooling. Further, flow does not exit the device through a port provided for laser emission, as in prior art, since this does not accomplish the goal of keeping the primary emission window clean while keeping the working surface cool.

A more interestingly approach than intra-cap flow cooling, alone, is one that uses a laminar flow (or flows) within a compound outer cap structure for more imitate cooling of the device at the tissue contact point, from within the working cap itself. This concept is really an extension of intra-cap flow cooling, but is a special case where the two cap surfaces are not provided by separate structures, but are afforded within a single, monolithic cap that provides a lumen of some type within to conduct coolant.

The monolithic cap with integral laminar flow channels functions because, though made through laminating layers of silica material, with thermal fusion, the cap is a separate component that may be annealed to remove the stresses of fusion fabrication. It is no more susceptible to thermal shock damage than a standard cap of prior art, dry, and with sufficient fluidic flow within the regions that are subjected to rapid thermal cycling by the interaction of the laser pulses with tissues, thermal stresses are greatly reduced over prior art.

The concept can be extended ad infinitum by utilizing a laminar flow cap with intra-cap flow as described previously, and by adding more layers of laminar flow. At some point, however, one reduces the structural integrity of the device as more and more volume that was previously silica is replaced with fluid flow channels, but even multiple thin wall silica layers, separated by fluid flow channels, may be of interest in some applications. As one silica barrier fails, flow is more concentrated in the damaged area by leakage through the new port formed by failure. Thin-wall failures are less likely to distort the laser output than thick-wall failures in that perforations through thin walls have more similar opening diameters on the outer and inner diameters.

Device output energy densities may be increased by forming curved bevel reflection surfaces (focusing mirrors), by reducing the maximum light propagation angles within the base fiber and/or at the fiber tip and by providing additional beam shaping glens surfaces at refractive index barriers throughout the design. A reflective metallic marker may be provided for a thermal stable orientation mark directly opposite the fiber output in fixed cap orientation embodiments.

Free rotation of the outer protective cap is provided in one embodiment to increase the surface area of tissue to cap contact throughout the surgery, further forestalling degradation onset, tissue adhesions and fiber failure. A scraping surface is provided on the tissue contact surface of one embodiment for enhanced removal (mechanical) of coagulated tissues, accumulations of which would otherwise reduce subsequent laser energy to tissue interaction.

Fusion of the inner protective cap is possible in this invention because the thin-wall harbors less internal stress than thicker caps required in single cap designs and because the thin-wall inner cap is not in contact with vaporizing tissues, but is shielded by the thicker working cap and insulated by either air (dry design) or fluid flows (wet designs).

"Fluid flow" embodiments of the new art also anticipate the use of non-aqueous fluids that offer greater transparency at the surgical wavelength, better heat transfer and/or more attractive refractive indices than aqueous fluids, e.g. fluorocarbon solvents. Further, materials that are not fluid or that become fluid at elevated temperature are also anticipated, such as amorphous fluoropolymers (e.g. DuPont Teflon AF 1600) and index matching gels.

Among the objects of the present invention are the following:

To provide a new and useful lateral fiber output termination for resistance to hydrothermal damage to energy delivery devices used in surgical procedures involving vaporization for removal of unwanted tissue;

To provide a new and useful lateral fiber output termination for resistance to devitrification damage to energy delivery devices used in surgical procedures involving vaporization for removal of unwanted tissue;

To provide a new and useful lateral fiber output termination for resistance to tissue adhesions in surgical procedures involving vaporization for removal of unwanted tissue;

To provide a new and useful lateral fiber output termination for resistance to thermal shock damage to devices in surgical procedures involving vaporization for removal of unwanted tissue;

To provide a new and useful lateral fiber output termination for resistance to photo-acoustic shockwave damage to deices in surgical procedures involving vaporization for removal of unwanted tissue;

To provide a new and useful lateral fiber output termination for improved energy to target tissue coupling efficiency in surgical procedures involving vaporization for removal of unwanted tissue;

To provide a new and useful lateral fiber output termination for improved energy density at target tissues in surgical procedures involving vaporization for removal of unwanted tissue;

To provide a new and useful lateral fiber output termination for improved aiming laser energy density at target tissue for enhanced orientation in surgical procedures involving vaporization for removal of unwanted tissue;

To provide a new and useful lateral fiber output termination for improved accessory orientation in surgical procedures involving vaporization for removal of unwanted tissue;

To provide a new and useful lateral fiber output termination for reducing collateral tissue damage about or near target tissue in surgical procedures involving vaporization for removal of unwanted tissue;

To provide a new and useful lateral fiber output termination for reduced scatter of therapeutic energy in surgical procedures involving vaporization for removal of unwanted tissue;

To provide a new and useful structure on lateral fiber output terminations for enabling concomitant mechanical removal of coagulated tissues in surgical procedures involving vaporization for removal of unwanted tissue.

The novel features that are considered characteristic of the invention are set forth with particularity in the appended claims. The invention itself, however, both as to its structure and its operation together with the additional objects and advantages thereof will best be understood from the following description of the preferred embodiment of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments of the invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

The present invention provides an improved optical fiber tip for laterally directing a laser beam. The present invention comprises a waveguide, such as an optical fiber, having a specialized output tip. Electromagnetic radiation is coupled into the waveguide and propagates in a propagation direction along the waveguide to the output tip (also known as working tip and distal tip, the energy source end of the waveguide being proximal), also referred to by surgeons as the "crystal" (a misnomer). The output tip includes a tissue contacting surface, preferably a substantially homogeneous transmission medium, with respect to refractive index, and a reflecting surface. The reflecting surface is disposed at an angle off normal to the propagation axis so that electromagnetic radiation is internally reflected in a lateral direction relative to the propagation direction, preferably through the substantially homogeneous transmitting medium toward a particular area on the tissue contacting surface. The electromagnetic radiation propagating in the lateral direction does not cross highly curved barriers of media with relatively large differences in refractive index such that beam profile distortions and reflections are minimized.

According to one embodiment of the invention, the waveguide includes an optical fiber having a beveled distal end. The distal end of the tip is beveled at an angle relative to the propagation direction of the radiation so that substantially all the radiation is internally reflected onto a particular area of the tissue contact surface. The beveled tip is fused within a thin primary capsule, item one of the lateral transmission medium, to preserve integrity of the barrier in refractive indices between the propagation medium and air or vacuum. The output surface of the thin capsule (primary cap, first cap or TIR preserving cap) may be machined normal to, or substantially normal to the central ray of the laterally reflected energy to minimize refraction at the capsule surface. A second, thicker capsule (tissue contact cap, working cap) is disposed about the primary capsule to perform the tissue contact function. The inner surface of the secondary capsule may be modified to a flat surface, substantially normal to the central ray of the reflected energy to minimize refractions at that surface.

According to another configuration of the invention, space between the primary and secondary capsules is filled with a fluid of substantially similar refractive index ($\Delta\eta<0.2$) to minimize refractions at the material barriers within the transmission pathway of the reflected light. Preferred fluids are air, water, aqueous solutions, optical gels and fluorocarbon solvents.

Figure 1A:
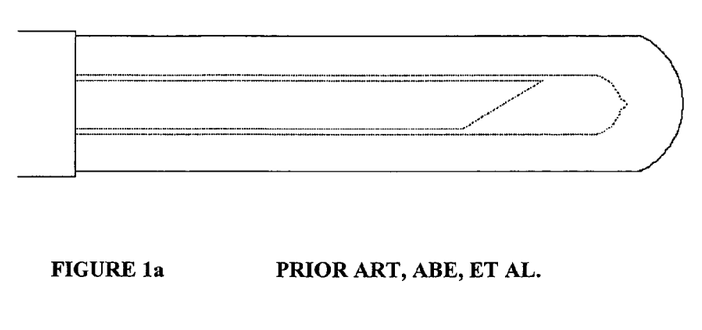
FIG. 1a and 1b is side view in section along the centerline of the prior art in Abe, et al., with a cross sectional view taken approximately at the center of the output plane.
Figure 1B:
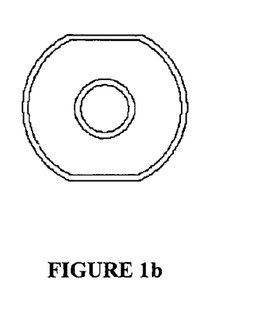
Figure 2A:
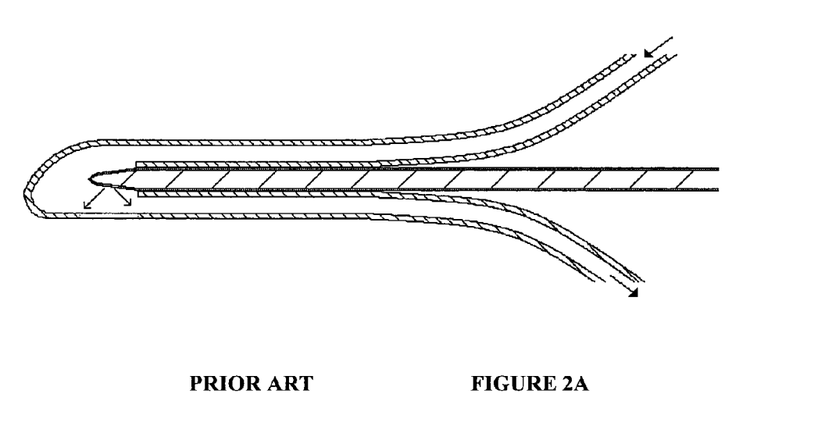
FIG. 2a and 2b is side view in section along the centerline of the prior art in Rowe, with a cross sectional view taken approximately just in front of the output plane.
Figure 2B:
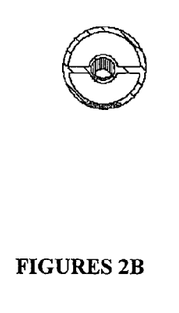
Figures 3A, 3B:
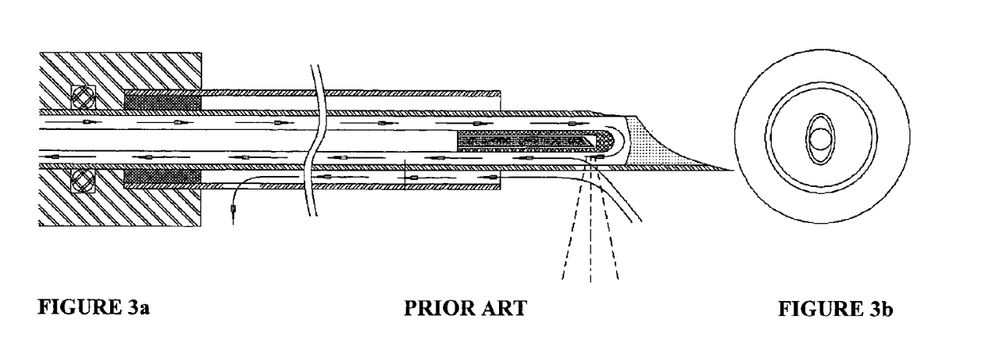
FIG. 3a and 3b is side view in section along the centerline of the prior art in Loeb, et al., with a cross sectional view taken approximately at the break in the side view in section.
Figure 4:
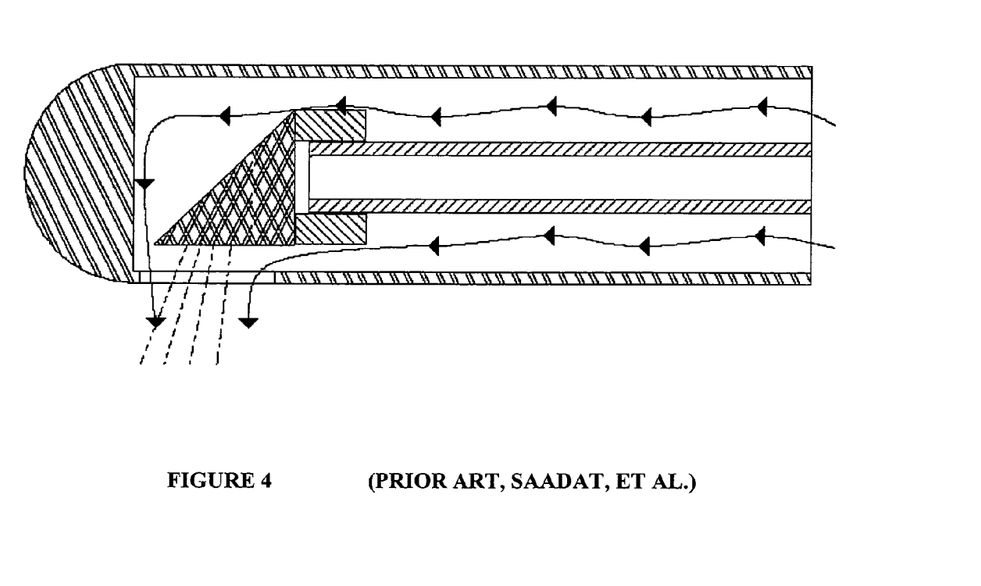
FIG. 4 is side view in section along the centerline of the prior art in Saadat, et al.
Figure 5A:
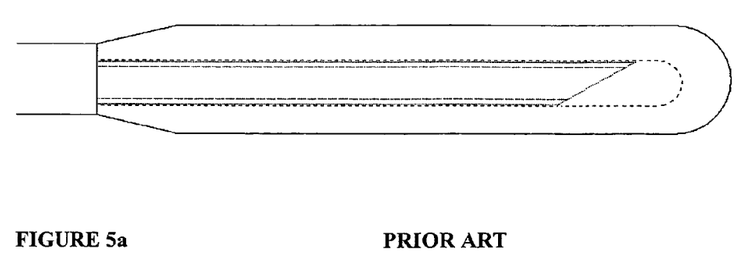
FIG. 5a and 5b is side view in section along the centerline of the prior art, marketed as GreenLight™, by Laserscope Surgical Systems Incorporated, and taught in Pon, with a cross sectional view taken approximately at the center of the output plane.
Figure 5B:
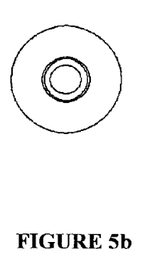
Figure 6:
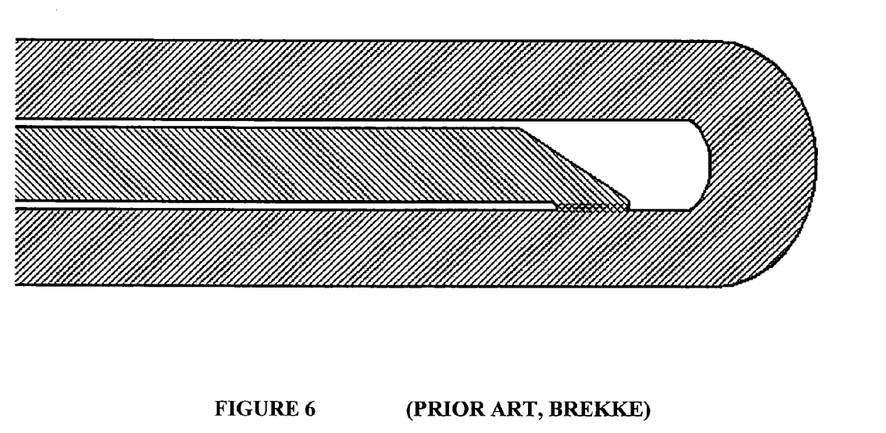
FIG. 6 is side view in section along the centerline of the prior art, marketed as ScaterFree™ by Laser Peripherals Incorporated, and taught in Brekke.
Figure 7:
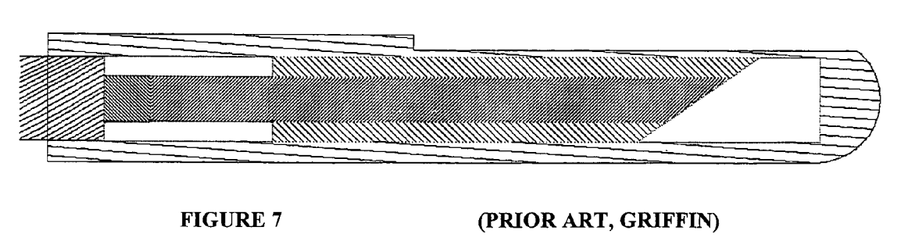
FIG. 7 is side view in section along the centerline of the prior art, marketed as MaxLight™ InnovaQuartz Incorporated and taught in Griffin.
Figure 8:
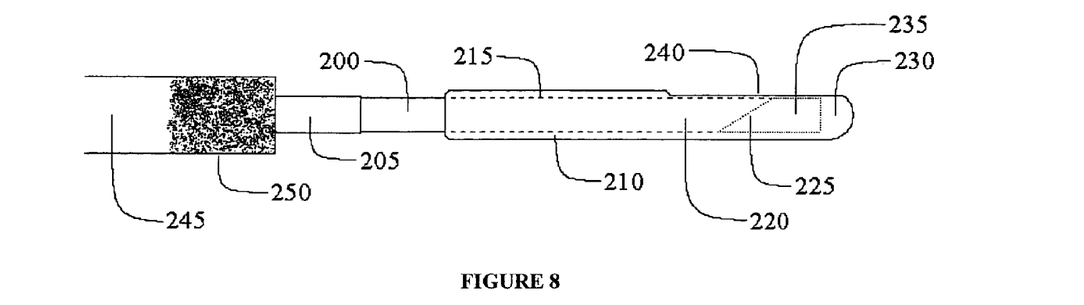
FIG. 8 is side view in section along the centerline of inner cap protecting the energy conduit.

A specific embodiment of the inner primary cap subassembly is depicted in FIG. 8, where the waveguide 200 is a silica core optical fiber, clad 205 with fluorine doped silica and coated with fluoroacryalte or fluorourethane and buffered 245 with a thick protective polymer such as polyamide, polyamide-imide, ethylene tetrafluoroethylene, or polyester elastomer, equipped with a beveled tip or reflective surface 225 where the distal portion or working tip 220 of the waveguide 200 is hermetically fused 215 within a thin silica primary capsule 210 to preserve the refractive index of medium 235 and protect the reflective surface 225. The buffer polymer 245 may be surface roughened 250 to promote adhesion at a later stage of assembly and an output surface 240 of the primary capsule 210 may be machined flat, to provide a planar surface substantially normal to the axis of a central reflected ray to minimize reflections and cylindrical refraction.

Figure 9:
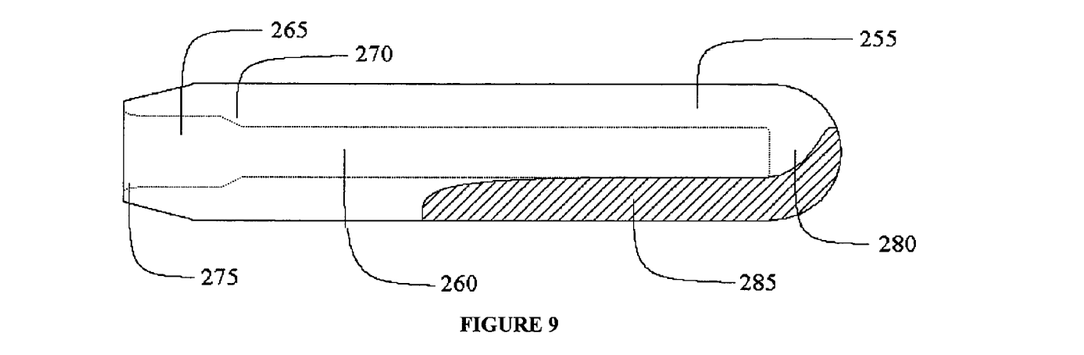
FIG. 9 is side view in section along the centerline of outer cap for tissue contact.

A simple embodiment of the outer, tissue contacting secondary capsule 255 is depicted in FIG. 9. The tissue contact function requires more substantial material bulk and thickness, owing to the extreme temperatures encountered in vaporizing tissues and the challenging chemical use environment presented by surgical applications. The secondary capsule 255 presents at least two bore diameters, a smaller bore diameter 260 and a larger bore diameter 265. The larger bore diameter 265 is proximal (at the opened end) and dimensioned to accept the roughened fiber buffer 250 and adhesive and gently reduces at 270 to the smaller bore 260 to facilitate loading of the optical subassembly 210 depicted in FIG. 8. A slight inner chamfer 275 on the larger bore 265 facilitates insertion of the roughened fiber buffer 250. A reflective metallic thin film orientation marker 285 is positioned opposite the tissue contact surface.

Figure 10:
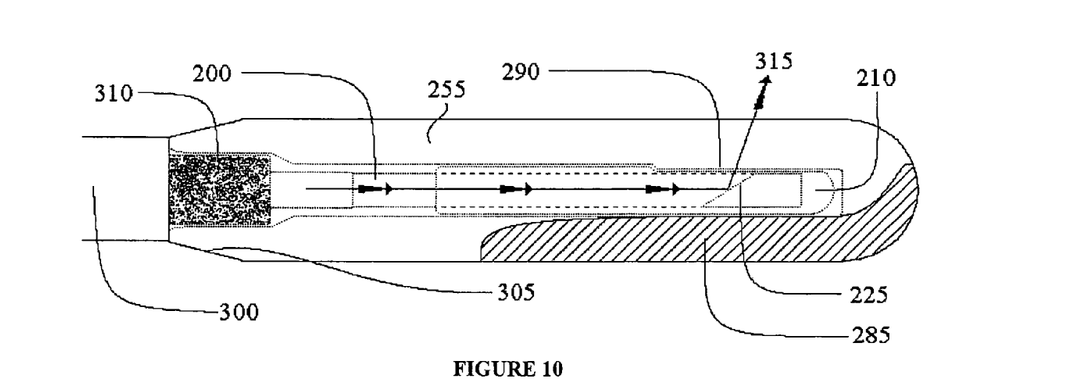
FIG. 10 is side view in section along the centerline the combined, dry embodiment of the invention.

FIG. 10 depicts the secondary capsule 255 of FIG. 9 as installed on the optical subassembly 210 of FIG. 8 where immobilization is provided by a thin film adhesive 310. The central light ray (zero order) within the waveguide 200 is depicted by the arrows 315 reflecting off the waveguide axis at the bevel tip 225. A secondary buffer 300, e.g. heat shrink tubing, may be applied over the section of the polymer coated waveguide 200 that is proximal to the working tip 220 to provide a smooth dimensional transition, through a secondary capsule outer chamfer 305, to a maximum device diameter. In this embodiment an optional flattened inner surface 290 of the secondary capsule 255, which is complementary to the output surface 240 of the primary capsule 210, is also depicted.

Total reflections and output spot distortion are greatly reduced by geometric means alone, through the elimination of curved surfaces within the transmitting pathway of the reflected beam 315. Rays that are not transmitted (reflections) generally impinge upon the metallic film orientation marker 285 and are redirected generally in the direction of the target tissue or are absorbed. The transmission efficiency of this simple embodiment is typically >95% as measured by lateral energy divided by axial energy with the lateral tip removed. At high average power or peak pulse energy, a gold film orientation marker 285 is damaged by the highest peak energy in the reflected beam, producing a burn through spot diameter roughly ½ of the output beam diameter and lateral efficiency is diminished by approximately 5% as reflection of the energy by the metallic film 285 is diminished.

In surgical use, a secondary capsule 255 that is in contact with tissue suffers damage, becoming frosted on the output surface beginning at approximately 20,000 Joules to approximately 100,000 Joules, depending upon the type of silica used and the surface quality at the tissue contact surface as well as the intimacy of tissue contact and motions across tissues, the laser beam qualities (CW, pulse, pulse width, repetition rate) the type and flow rate of irrigation fluid used, the tissue type and other factors outside the control of the device designer. Catastrophic failure, where the frosted output erodes sufficiently to perforate the secondary capsule 255, has not been observed for this embodiment up to 400,000 Joules delivered at 76 W average power, 2120 nm. Failure of the adhesive seal 310 to exclude irrigation fluid has been observed with as little as 100,000 Joules delivered, but due to the presence of the primary capsule 210 the lateral emission function is preserved and performance actually increases due to further reductions in reflections and refractions within the device provided by the closer index match of the irrigation fluid to silica with respect to air.

It was thought that the aqueous fluid between the secondary capsule 255 and the primary capsule 210 would absorb sufficient infrared energy to explosively vaporize were the secondary capsule seal 310 to fail, but this has not been observed, even where the device is removed to air and fired (for the purpose of measuring residual lateral efficiency on a power meter). The thickness of the fluid within the reflected beam transmission pathway is apparently too thin to absorb enough laser energy to boil enough liquid to cause expansion sufficient to cause structural failure.

Figure 11:
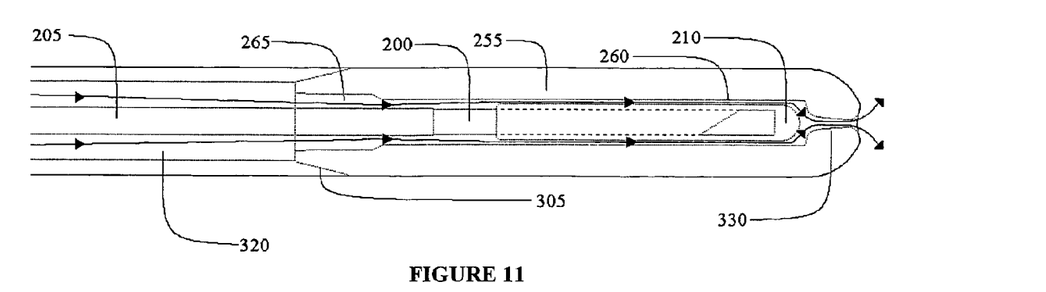
FIG. 11 is side view in section along the centerline of the conceptually simplest of the fluid cooled embodiments of the invention.

In a preferred embodiment of the invention, FIG. 11, the fiber buffer (245 in FIG. 8) is missing (removed) or is substantially thinner than standard and the waveguide 200 is housed within a coaxial conduit or accessory cannula channel 320, e.g. a polymer or metallic tube that is secured to the secondary capsule 255 with solder or adhesive at the outer diameter chamfer 305. Fluid may be coupled by tapping the surgical irrigation inlet of endoscopic equipment or by a separate source or through a standard "T" fitting, such as those well known in the art. Fluid is conducted through the accessory cannula 320 channel, into the secondary cap proximal bore 265 and about the fiber subassembly, to be released though a distal port 330 into the surgical field. The primary capsule 210 transmitting surface and secondary capsule receiving surface 260 (inner diameter) may possess the machined flats describer earlier, (240 and 290 in FIGS. 8 and 10, respectively), but owing to the closer refractive index match of the irrigation fluid to the silica structures, such geometric mechanisms for reducing refraction and reflection are not strictly necessary.

Figures 12A, 12B:
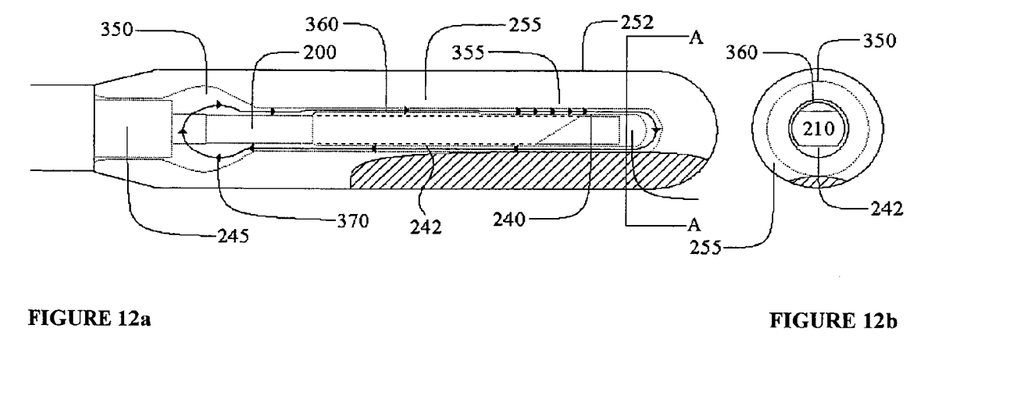
FIG. 12a and 12b is a side view in partial section along the centerline of a sealed, fluid cooled version of the device, with a cross sectional view taken just distal to the output plane.

Another potential embodiment is the sealed coolant system depicted in a FIG. 12a and FIG. 12b. The cooling fluid need not be aqueous in this embodiment but may be a fluorocarbon heat transferring fluid or other liquid. A fluid reservoir is provided within the device, depicted as machined within the secondary capsule 255 bore at 350, but a reservoir within an auxiliary cannula, proximal to the lateral assembly, would also function. In the depicted embodiment, the output surface of the primary capsule 210 cap is machined flat 240 but less for geometric reduction of reflection and refraction than for producing a directional, heat driven fluidic flow. The original primary capsule 210 surface is preserved 360 for some portion of the cap length on the output side to serve as a flow restrictor. The opposite side of the inner cap is also machined flat 242, but along the entire cap length to provide a free fluid flow channel. As in FIG. 10, the fiber buffer 245 forms the primary seal between the surgical environment and the interstitial space between the primary and secondary capsules, 210 and 255. As tissue is vaporized, the tissue contacting surface 252 of the secondary capsule 255 heats and the heat is conducted through the thickness of the secondary capsule to the fluid in the transmitting pathway of the reflected beam (closely spaced arrows). The interstitial fluid expands and preferentially advances distally, away from the flow restriction 360, around the tip of the primary capsule 210 to the fluid reservoir 350, where it cools and replenishes flow through the restriction 360, i.e. a cyclic coolant circuit is established as depicted by the arrows.

Figure 13:
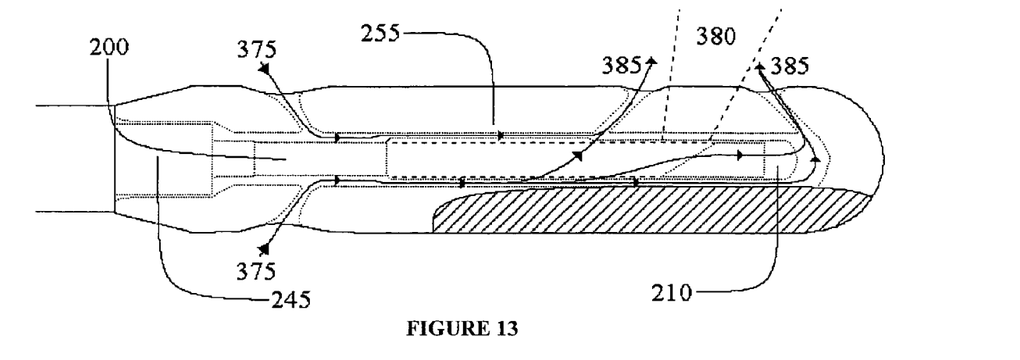
FIG. 13 is a side view in section along the centerline of one port arrangement for the optically pumped, surgical irrigation variant of the device.

Another embodiment for providing interstitial cooling may be provided as depicted in FIG. 13, where surgical irrigation fluid from around the fiber in the use environment is drawn in through proximal ports 375 in the secondary capsule 255 and exhausted through distal ports 385 surrounding the lateral transmission pathway 380. This embodiment is a close simulation of the leaking fibers that were referenced above.

Regardless of the laser wavelength used in vaporization, some tissue beneath the vaporization plane is killed but not removed. The term of art for this is affect of laser energy on tissue is coagulation. Coagulated tissues present far different absorption characteristics with respect to live tissues such that the initial, highly efficient vaporization pass is typically followed by a somewhat less efficient second pass, which is followed by a third pass at possibly lower efficiency, ad infinitum, because less efficient absorption of the laser energy leads to less vaporization and more underlying coagulation. The decrease in vaporization efficiency is not self-accelerating, but progresses modestly as approximated by first order kinetics.

Figure 14:
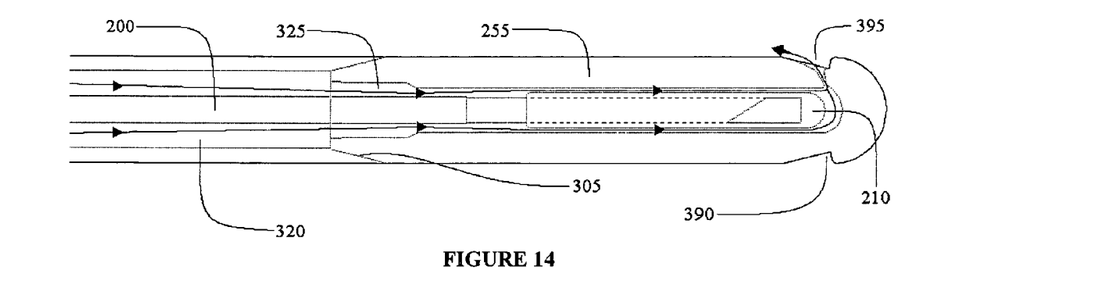
FIG. 14 is a perspective view of one alternative for distal fluid release in active delivery (surgical irrigation tap) to provide additional cooling and cleanliness for the outer diameter of the tissue contacting cap while providing mechanical morcellation of bound coagulated tissues below the vaporization plane.

FIG. 14 depicts an alternative embodiment designed to mediate this problem: a distal port arrangement 395 whereby the exiting coolant is made to pass over surfaces that are prone to contamination by tissues and that become labile to damage where such contamination adheres. This embodiment is also equipped with a scraping device 390 for tissue morcellation concomitant with vaporization. To prevent build-up of tissues within the scraper, adjacent to the laser output surface ("lase output") on the outer cap, a port 395 is provided to constantly flush the scraper and the lase output, keeping them clean.

Figure 19:
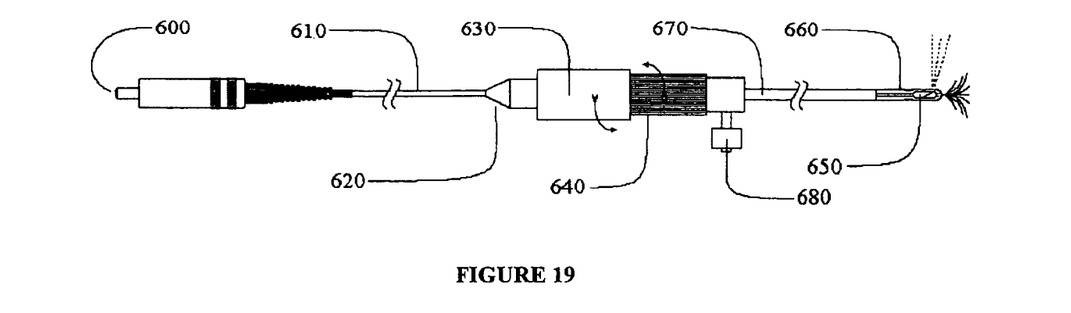
FIG. 19 is a view of a complete preferred embodiment device with primary and secondary cap relative rotation and cap interstitial cooling.

All lase outputs of silica capped fibers degrade in time, limiting the useful lifetime. Many of the variables that affect the onset and acceleration of the degradation are outside the control of the device design, as mentioned earlier. For surgical cases and applications where protracted capsule to tissue contact is required, with little or slow motion (fiber output relative to tissue), even the best possible fiber design will degrade and may become useless before the surgical goals are realized, necessitating the use of a second, fresh fiber for completion of the surgery. One strategy to avoid this is to provide the device in FIG. 11 with a turning mechanism at the proximal end of the fluid conduit cannula, outside the body and endoscopic channel port. A device as simple as an indexing holder 620, 630 and 640, depicted in FIG. 19 enables rotation of the secondary capsule 255 relative to the primary capsule 210 to be accomplished from outside the body, via the fluid conducting conduit 670, while the fiber remains positioned in the surgical field. Laser energy is coupled at 600, propagates distally along the waveguide 200 that is affixed to the proximal half of the rotating device 630 at 620, passes freely through the second half of the rotating device 640 to which the fluid conduit 670 is affixed, to the working tip as described elsewhere. Fluid is supplied by a Luer 680 or other connector within the rotation device or via ports within the cannula 670 just inside the fluid seal of the working channel port of the endoscope.

Figures 15A, 15B:
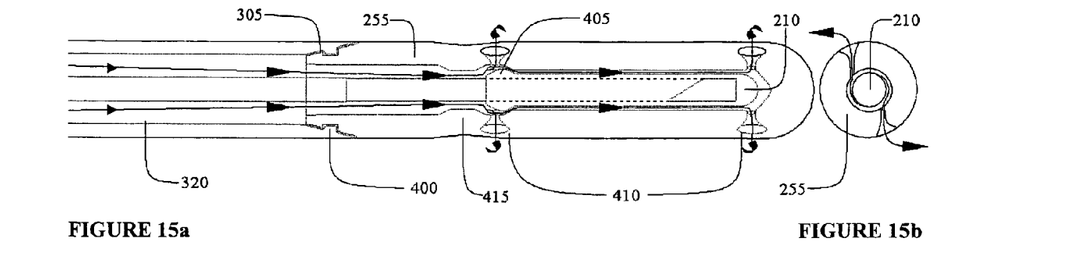
FIG. 15a and 15b is a perspective view of an alternative for distal fluid release that provides hydraulically driven rotation of the outer cap, where a rotary joint is provided.

Alternatively, given the presence of fluid flow in the device, exhaust ports 410 in the secondary capsule 255 may be arranged to function as jets, imparting rotational motion to the cap when it is not in tissue contact (or preferably, if forceful enough, even during tissue contact). FIG. 15 depicts such a concept where a rotating joint 400 is provided between the fluid transport cannula 320 and the outer secondary capsule chamfer 305 and a second point of centering is provided by a bulge 405 in the primary capsule 210, captured with a restriction in the outer cap bore 415 and equipped with exhaust ports 410 to insure that dynamic flow cushions the fiber rotation.

To insure continuous rotational motion, even in tissue contact, the fluid conduit cannula 320 can be equipped with a drive system proximal to the deepest point of endoscopic penetration, e.g. ~18' to 24' from the working tip. This drive system is preferably hydraulic drive from fluid flows, if adequate to the task. Alternatively, low cost, low voltage electric motors and gear drives can be assembled into a relatively small accessory handle on the fiber assembly, akin to the disposable electric tooth brushes now available: both continuous rotation and waggle about some portion of the full circle would be of benefit in reducing tissue adhesion problems and in spreading the damage across a larger secondary capsule 255 surface area.

Figure 16:
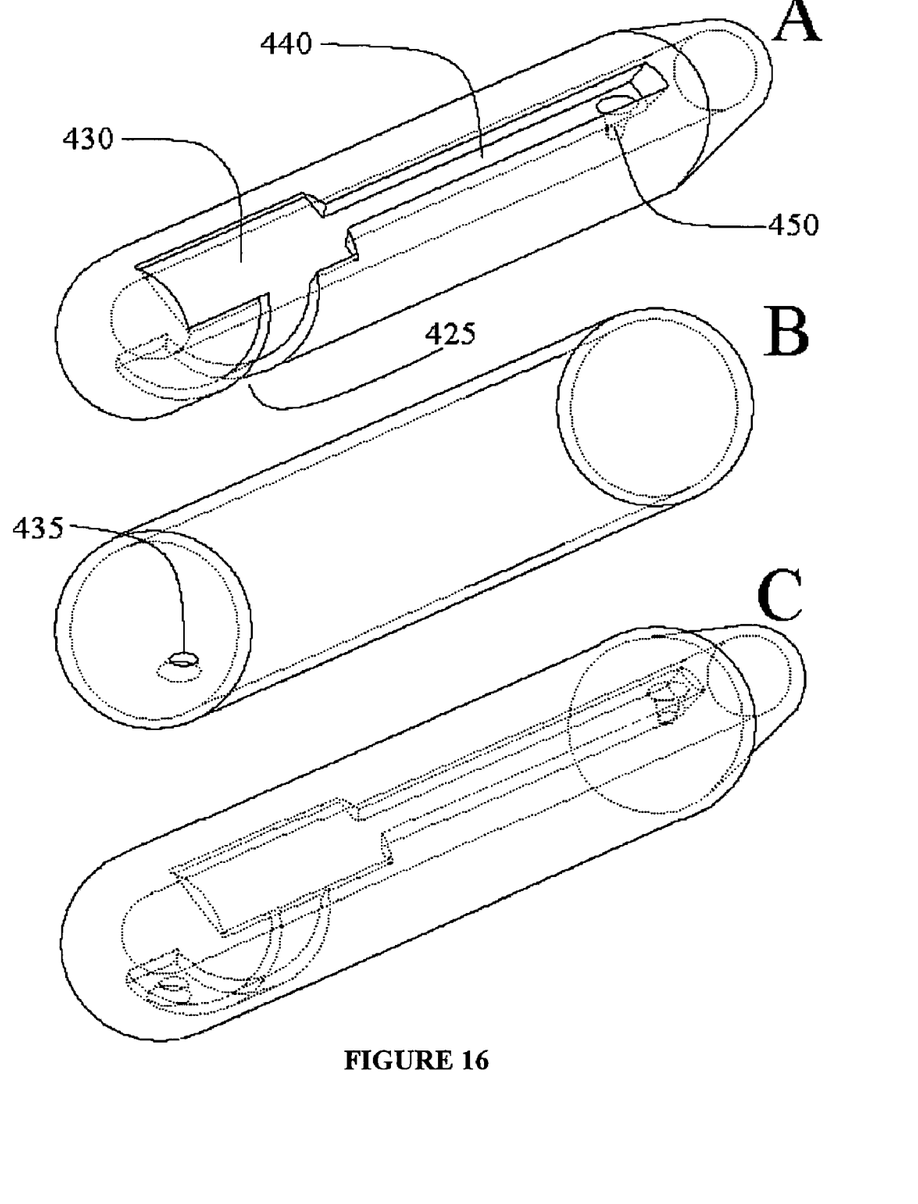
FIG. 16 is perspective view of a laminar flow monolithic secondary cap before fusion of two layers (A and B) and after fusion (C).
Figure 17:
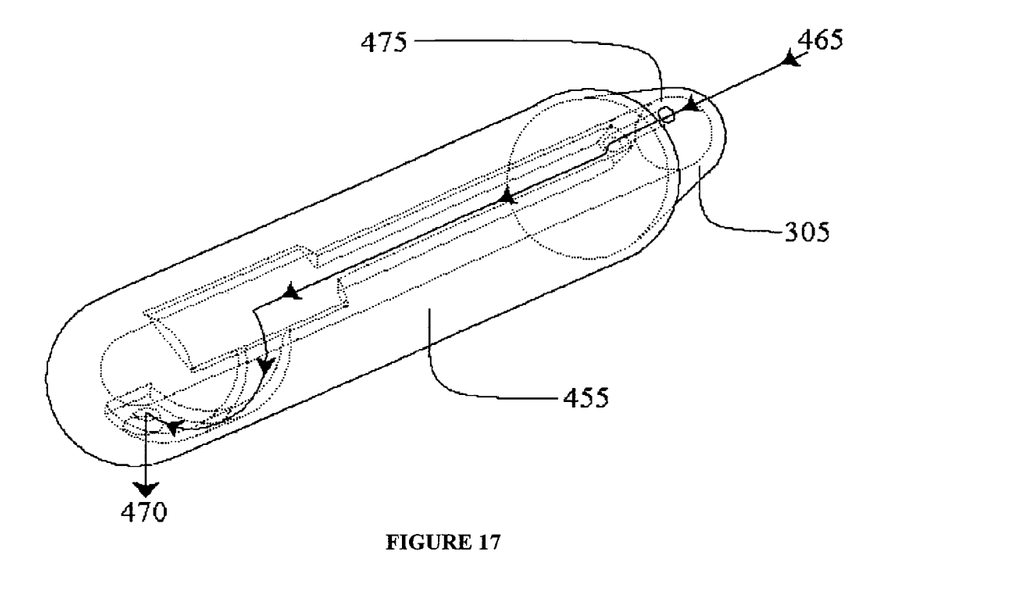
FIG. 17 is a perspective view of an alternative fluid source monolith depicting the fluid pathway.

Other embodiments of the secondary capsule 255 may take myriad forms, such as that depicted as nesting components (A & B, cap with channel circuit and sleeve, respectively) and as the final tissue contact cap assembly, C, in FIG. 16. Beginning near the proximal chamfer 305, a groove 440 is machined in the surface of the cap inner structure A, extending distally to the transmission pathway, where it expands to a plane 430 encompassing enough area to cover the entire beam path. A fluid access port 450 is drilled through the cap wall to the inner diameter and an exhaust groove conduit 425 is machined about the circumference to the opposite side of the cap. A thin wall silica sleeve B is equipped with an exhaust port at 435 and positioned on cap A such that the exhaust port 435 aligns with the circumferential fluid conduit 425. The two pieces are fused to form a monolithic cap C with internal fluid conduits. When assembled onto an optical subassembly FIG. 8 as depicted in FIG. 17, the composite cap 455 substituting for the tissue-contacting cap 255 depicted in FIG. 11, the alternative inlet port 475, formed on the proximal chamfer 305 of the composite cap, permits a portion of the fluid flow to be directed just below the tissue-contacting surface for additional cooling.

Figure 21:
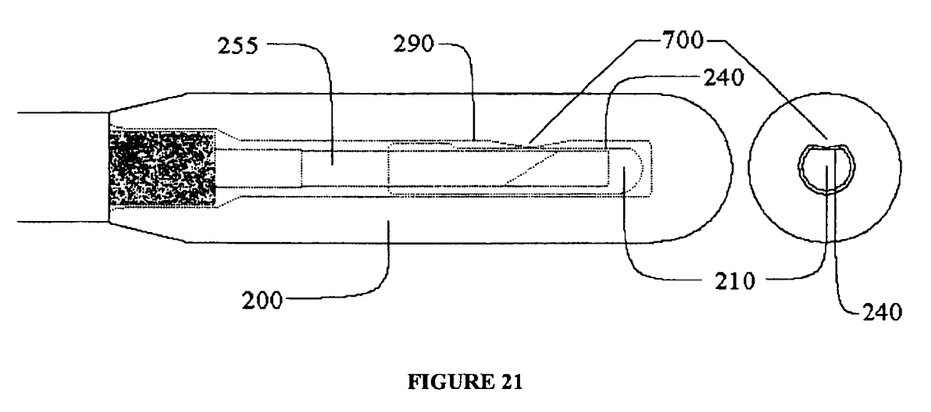
FIG. 21 is a side view in section along the centerline with a beam conditioning lens formed on the inner wall of the tissue contacting cap.

Further, the production of additional refractive index transitions, albeit-minor, does offer the potential for adding some additional beam conditioning optical surfaces to the structure, e.g. a meniscus-like lens penetrating the planar fluid conduit within the transmission pathway will reduce the divergence of the output slightly as depicted in FIG. 21 for such a lens 700 formed on the inner wall 290 of a standard tissue contacting cap 255.

Figure 18:
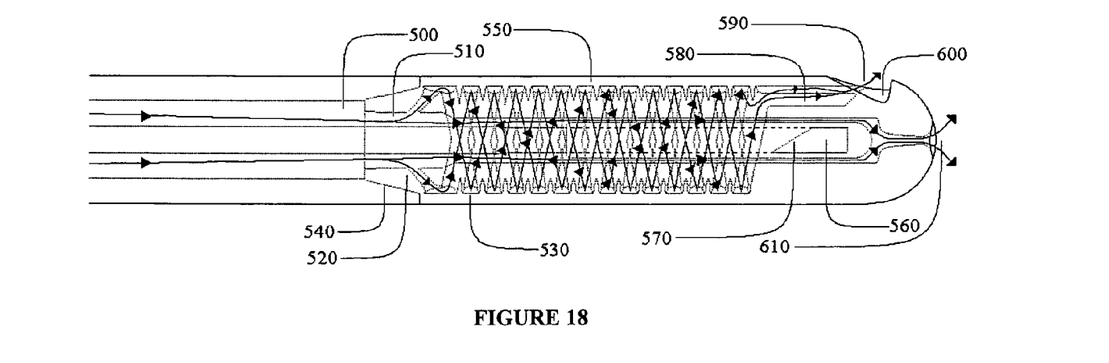
FIG. 18 is a side view in partial section of a double helix, crossed channel laminate cap equipped device for maximum flow in the outer coolant plane: the preferred embodiment for dual flow cooling in the device.

FIG. 18 depicts a version of the assembly with integral cooling channels that are simple to fabricate and represents a preferred embodiment of the device. Helical grooves 530 are machined in the outer diameter of the inner portion of the composite secondary capsule 455, for example under indexed rotation with a $CO_2$ laser. As the grooves 530 near the distal end of the secondary capsule 455, at about the area of beam passage, rotation is ceased to form a flat 580 on one side of the secondary capsule 455 inner structure's outer diameter. The index direction is reversed until the beam approaches the beginning of the helix, where rotation is once again begun (same direction of rotation), forming a second helical pathway overlapping the first that results in what has been called a "diamond" pattern (for the diamond shaped islands of residual glass at initial diameter). Fluid access ports 520 are drilled at the proximal extremes of the helices and the inner structure is again sleeved with a thin walled silica cylinder 550 to form a semi-laminar channel about the entire circumference of the cap that is supported by the diamond shaped islands of silica, fused to the outer sleeve 550 and about the planar channel at the beam pathway. The cap is then melted to almost seal the distal end, forming the port for interstitial cooling flow outlet 610. A tissue morcellating blade 600 is machined just proximal to the cap tip and distal to the beam path and the laminar cap flow outlet port 590 is drilled through the blade surface to the distal portion of the planar laminar conduit.

The optical subassembly 210 as depicted in FIG. 8 is inserted within the composite secondary capsule 455 thus formed, with the TIR bevel 570 oriented to place the beam path directly in the center of the planar laminar fluid conduit. A polymer cannula is affixed to the proximal cap chamfer 540 with adhesive. Fluid provided within the polymer conduit 500 couples to the interstitial space between the inner cap and outer cap as laminar flow within the composite outer cap, as depicted by the arrows. A gold film reflector and orientation marker may be provided as depicted in earlier figures.

Further control of the output quality of the device may be provided by incorporating other art within the design, such as TIR bevel surfaces with a slight curvature, for focusing the output beam onto tissues. Other aspects and advantages of the present invention can be seen upon review of the figures, the detailed description, and the claims which follow. The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. An apparatus for communicating and laterally directing electromagnetic radiation, comprising:
   a. a waveguide for communicating electromagnetic radiation having a distal tip with a bevel for redirecting the electromagnetic radiation in a lateral direction;
   b. a primary capsule that is attached over the distal tip of the waveguide;
   c. a secondary capsule that is attached over the primary capsule and distal tip combination;
   d. where the primary capsule and secondary capsule are separated by a space; and
   e. wherein the space is filled with a medium that matches the index of refraction of the primary capsule to the secondary capsule.

2. The apparatus according to claim 1 wherein the index matching medium is selected from the group consisting of air, water, aqueous solutions, optical gels, fluorocarbon solvents and polymers.

3. The apparatus according to claim 1 wherein the index matching medium filled space between the primary capsule and the secondary capsule is sealed and the index matching medium is relatively static.

4. The apparatus according to claim 1 wherein the index matching medium filled space between the primary capsule and the secondary capsule is sealed and the index matching medium is mobile, moving by convection.

5. The apparatus according to claim 1 wherein the index matching medium filled space between the primary capsule and the secondary capsule further comprises an output port and the index matching medium flows between the primary capsule and secondary capsule and out the output port, said flow being accomplished by external pressure.

6. The apparatus according to claim 1 further comprising an output port in the secondary capsule, wherein the output port is in a position capsule where fluid outflow is directed over a tissue contacting surface of the secondary capsule.

7. The apparatus according to claim 1 wherein the index matching medium filled space between the primary capsule and the secondary capsule is open and the index matching medium flows between the primary capsule and secondary capsule, said flow being accomplished by optical pumping.

8. The apparatus according to claim 1 wherein the secondary capsule is replaceable as a separate component.

9. The apparatus according to claim 1 wherein the secondary capsule is rotatable.

10. The apparatus according to claim 9 wherein the rotation of the secondary capsule is substantially continuous.

11. The apparatus according to claim 1 where the secondary capsule further comprises a tissue morcellation blade.

* * * * *